(12) United States Patent
Peterson et al.

(10) Patent No.: US 8,139,220 B2
(45) Date of Patent: Mar. 20, 2012

(54) POINT-OF PURCHASE (POP) SPECTROPHOTOMETER FOR OPEN-VIEW MEASUREMENT OF A COLOR SAMPLE

(75) Inventors: Steven H. Peterson, Martin, MI (US); Peter G. Vander Jagt, Belmont, MI (US); David A. Salyer, Ada, MI (US)

(73) Assignee: X-Rite, Inc., Grand Rapids, MI (US)

( * ) Notice: Subject to any disclaimer, the term of this patent is extended or adjusted under 35 U.S.C. 154(b) by 525 days.

(21) Appl. No.: 12/211,395

(22) Filed: Sep. 16, 2008

(65) Prior Publication Data

US 2010/0067009 A1   Mar. 18, 2010

(51) Int. Cl.
*G01J 3/46* (2006.01)

(52) U.S. Cl. ......................................................... 356/402

(58) Field of Classification Search ........... 356/402–425
See application file for complete search history.

(56) References Cited

U.S. PATENT DOCUMENTS

| | | | |
|---|---|---|---|
| 4,678,325 | A | 7/1987 | Lehtikoski et al. |
| 6,888,633 | B2 | 5/2005 | Vander Jagt et al. |
| 7,092,097 | B2 | 8/2006 | Cargill et al. |
| 7,145,657 | B2 | 12/2006 | Peterson et al. |
| 7,262,853 | B2 | 8/2007 | Peterson et al. |
| 2006/0192957 | A1* | 8/2006 | Frick et al. ................... 356/328 |
| 2007/0291993 | A1 | 12/2007 | Nisper et al. |
| 2008/0002204 | A1* | 1/2008 | Xu et al. ....................... 356/418 |

FOREIGN PATENT DOCUMENTS

JP          03131742          6/1991

OTHER PUBLICATIONS

CFS57CA / CF57CA Countertop Spectrophotometer Specification Sheet (Jul. 2006)—1 page.
http://www.xrite.com/product_overview.aspx?ID=286 website for CounterTop 700—1 page.
GretagMacbeth product literature, ColorEye XTS Satellite Spectrophotometer, 1 page.
http://www.xrite.com/worldwide.aspx, 1 page.
http://www.datacolor.com/spectrophotometers/check/, 3 pages.
http://www.datacolor.com/spectrophotometers/110/, 1 pages.
http://www.datacolor.com/spectrophotometers/110p/, 1 page.
http://www.datacolor.com/spectrophotometers/400/, 2 pages.
http://www.datacolor.com/spectrophotometers/550/, 2 pages.
http://www.datacolor.com/spectrophotometers/600/, 2 pages.
http://www.datacolor.com/spectrophotometers/650/, 2 pages.
http://www.byk.com/instruments/products/color_solidcolor_spectro-guide_1_US.php, 5 pages.
European Extended Search Report dated Mar. 24, 2010.

* cited by examiner

*Primary Examiner* — Gregory J Toatley
*Assistant Examiner* — Abdullahi Nur
(74) *Attorney, Agent, or Firm* — McCarter & English, LLP

(57) ABSTRACT

Disclosed herein is a point-of-purchase (POP) spectrophotometer for open-viewing of a color sample. The POP spectrophotometer includes a housing assembly containing an illumination optical system and an imaging optical system in desired orientation. Also provided is at least one of a second illumination optical system, a sheen detection system, and a camera system. The housing assembly includes a chassis in secure arrangement with a plurality of supports that define a target plane having a target location and that space the chassis therefrom. The chassis is configured to position the illumination, imaging, sheen detection, and/or camera systems in desired orientations relative to the target location and each other. The POP spectrophotometer can include an alignment device and/or targeting optics for facilitating user-identification of the target location, and means can be provided to enhance insensitivity to ambient light and/or depth variation of the color sample.

20 Claims, 13 Drawing Sheets

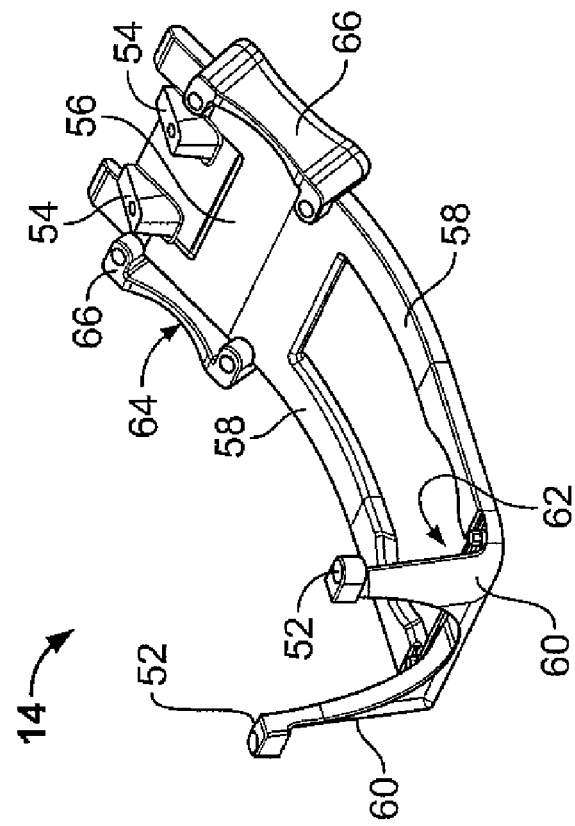
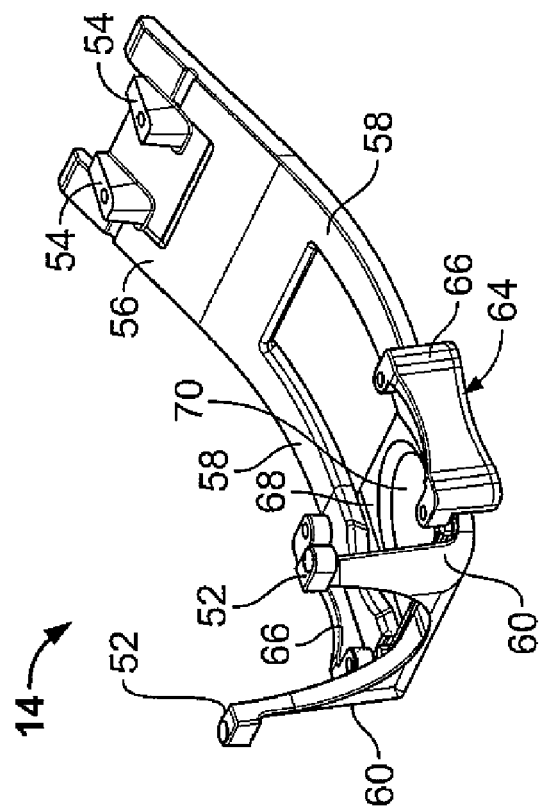

POINT-OF PURCHASE (POP) SPECTROPHOTOMETER FOR OPEN-VIEW MEASUREMENT OF A COLOR SAMPLE

FIELD OF THE INVENTION

The present invention relates generally to spectrophotometers for measuring the color of a color sample. In particular, exemplary embodiments of the present invention relate to a spectrophotometer especially suitable for use at a point of purchase (POP) to undertake open-view measurements of color samples having disparate physical dimensions.

BACKGROUND OF THE INVENTION

It is known in the art to provide spectrophotometers for measuring a color sample. For example, reference is made to commonly-owned U.S. Pat. App. Pub. No. 2008/0002204 (the "'204 Publication"), the contents of which are incorporated herein by reference for all permissible purposes. The '204 Publication discloses a color measurement device for use at various stages of industrial processes. The device of the '204 Publication offers enhanced insensitivity to ambient light, measurement depth variations, and/or ambient temperature variations. The device of the '204 Publication may be embodied as an LED-based color measurement spectrophotometer. In the device of the '204 Publication, over-illumination in full-spectrum of the target object facilitates effective color measurements over varying depths of view, and collected light is measured at discrete wavelengths across the entire visual spectrum. The hardened, rugged design and packaging of the measurement device of the '204 Publication allows color measurement to be performed at various stages of industrial processes, and the device can add value by enabling enhanced detection of color errors.

The device of the '204 Publication and other spectrophotometers can incorporate numerous advantageous features. For example, reference is made to commonly-owned U.S. Pat. No. 6,888,633, the contents of which are incorporated herein by reference for all permissible purposes. The device of the '204 Publication can include a synchronous modulation-demodulation scheme in connection with the illumination and collection optics. Spectrophotometers can incorporate such advantageous features as LED thermal stabilization, light-emitting diode (LED) illumination, amplification features, minimizing sensitivities to depth variation, and other features discussed in commonly-owned U.S. Pat. No. 7,262,853 and those divisional applications thereof (now commonly-owned U.S. Pat. Nos. 7,092,097 and 7,145,657), the contents of all of which are incorporated herein by reference for all permissible purposes.

Prior art point-of-purchase (POP) spectrophotometers for retail consumer use have typically included closed-viewing chambers for measuring a color sample. For example, as shown in FIGS. 1A and 1B of the present application, a prior art POP spectrophotometer is shown that might typically be used at a retail paint store for color matching. One hand of a user is typically required to pivot open a stop between an open and closed position, while, at the same time, another hand of the user is required to insert a planar color sample between the stop and internal optics. Moreover, the color sample typically comes in physical contact with components of the prior art POP spectrophotometer, thereby making it difficult to measure wet color samples. As also shown, the color sample is conventional, being formed of a piece of paper with color disposed thereon.

Retail and other consumers of architectural paint, for example, whether they be professional painter or merely an everyday do-it-yourselfer, have come to expect the ability to get instant and exact matches to any color sample they provide at the point-of-purchase—even if the color sample cannot fit in a conventional sample holder or has surface qualities that defeat the measurement geometries of traditional instrumentation. Custom paint formulation is now the common expectation rather than the differentiating exception.

What is needed in the art is a spectrophotometer with enhanced ease of use to overcome these and other disadvantages.

SUMMARY OF THE INVENTION

The present invention overcomes the disadvantages and shortcomings of the prior art by providing a point-of-purchase (POP) spectrophotometer and/or a chassis thereof for open-view measurement of a color sample.

In a first aspect of the present invention, a housing assembly is provided for a POP spectrophotometer for open-viewing of a color sample. The housing assembly can include a chassis and support(s), such as a plurality of extensions, for supporting the chassis on a surface to define a target plane and space the chassis (and any optical systems thereof from the target plane for open-viewing of the target location. The supports can have a first end in secured relationship with the chassis, such as by being integrally formed therewith, fastened thereto, etc., and a second end configured to define a target plane with a target location, e.g., a location at which a color sample is to be positioned. A color sample can comprise a sheet of paper with color disposed therein. However, because the POP spectrophotometer preferably utilizes open viewing, it is contemplated that the color sample can comprise additional or alternative structures, such as a piece of a door, wood, wallpaper, curtain, an automobile body component, musical instrument, etc.

In a second aspect of the present invention, an alignment device is provided in secured relationship with the housing assembly and for facilitating user-identification of a target location of the target plane. In aspects of the inventions that incorporate electronics/optics for depth-insensitivity, the alignment device is further configured to be spaced apart from the target plane by that magnitude of distance, e.g., depth, by which the POP spectrophotometer is depth-insensitive.

In a third aspect of the present invention, the housing assembly is configured to contain and position an illumination optical system and an imaging optical system in suitable arrangement for sensing the color of an open-viewed color sample at any suitable depth at the target location of the target plane. In some aspects of the invention, the housing assembly can be configured to further contain and position (in desired arrangement with the illumination optical system and the imaging optical system) at least one of the following: (i) a second illumination optical system; (ii) a sheen detection system; and (iii) a camera system.

In a fourth aspect of the present invention, the imaging optical system can be provided with a targeting optical system. The targeting optical system preferably includes a light source, such as a light-emitting diode (LED) ring, and preferably further includes a switchable aperture assembly proximal the image plane of the imaging optical system. The switchable aperture assembly can include a first aperture of a first size, e.g., radius, and a second aperture of a second size, e.g., radius, different than the first size of the first aperture. The imaging optical system has a line of sight, and the LED ring can be positioned in-line with respect to components of the imaging optical system. The switchable aperture assembly can be positioned so as to alternatively switch the first and second apertures in-line as such. The imaging optical system can be provided such that the selected aperture substantially simultaneously (i) functions as a stop to at least partially define the perceived target size at the image plane, and (ii) reflects and/or projects light of the LED ring toward the target plane so as to facilitate user-identification of that target location size which corresponds to the perceived target size defined at the image plane.

Additional features, functions and benefits of the disclosed POP spectrophotometer and methods of use shall be apparent from the detailed description which follows, particularly when read in conjunction with the accompanying figures.

BRIEF DESCRIPTION OF THE DRAWINGS

For a more complete understanding of the present invention, reference is made to the following detailed description of exemplary embodiment(s) considered in conjunction with the accompanying drawings, in which:

FIG. 6A is a perspective view of the alignment device in the first or "calibration" position of FIG. 2;

FIG. 6B is a perspective view of the alignment device in the second or "viewing" position of FIG. 3;

DETAILED DESCRIPTION OF EXEMPLARY EMBODIMENT(S)

Figure 1A:
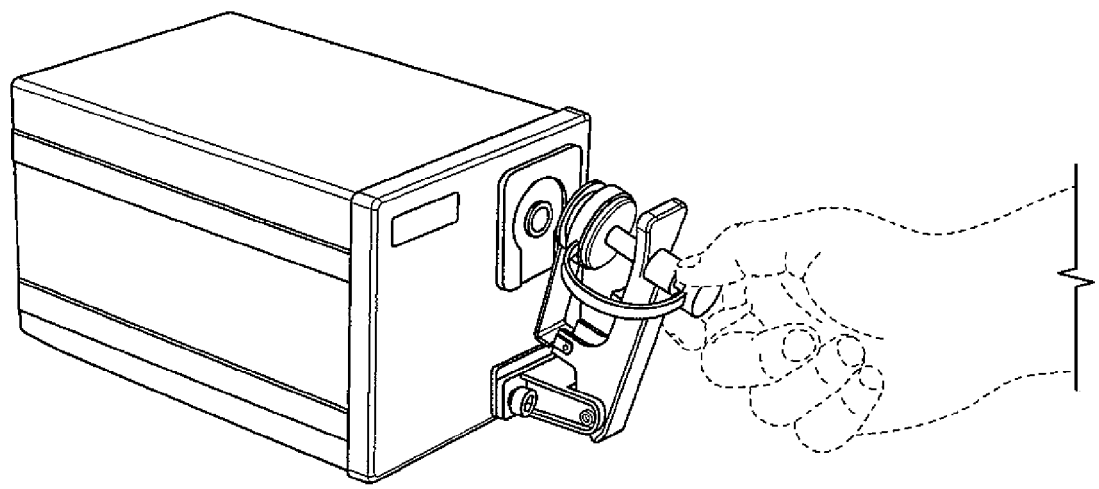
FIG. 1A is a perspective view of a prior art point-of-purchase (POP) spectrophotometer having a closed viewing chamber for receiving a color sample, the POP spectrophotometer being shown without a color sample and with a stop in a first position.

With reference to FIGS. 2-16, a point of purchase (POP) spectrophotometer 10 constructed in accordance with an exemplary embodiment of the present invention shall be discussed. As presented with further detail below, the POP spectrophotometer 10 includes a housing assembly 12, an alignment device 14, and a plurality of optical systems and associated electronics. The housing assembly 12 includes a chassis 16, a plurality of supports 18, a lid 20, and a plurality of securing elements 22a, 22b. The optical systems and associated electronics include a plurality of illumination optical systems 24a, 24b, an imaging optical system 26 that includes a targeting optical system 28 (e.g., sub-system), a sheen detection system 30, and a camera system 32.

A. The Housing Assembly and Alignment Device

Referring to FIGS. 2-7, 11, and 14-16, certain mechanical aspects of the present invention shall be discussed with further detail. The heading above, e.g., "The Housing Assembly and Alignment Device," and other headings herein are provided for the purposes of clarity of discussion, and shall not be considered limiting.

It is shown that the housing assembly 12 preferably includes a chassis 16, a plurality of supports 18, a lid 20, and a plurality of securing elements 22a, 22b. The housing assembly 12 is preferably formed of a rugged material, such as cast metal or plastic, and forms an enclosed area for securingly containing the electronics, optics, etc. The housing assembly 12 is compact, portable, and can have ornamentation disposed thereon. It is contemplated that the housing assembly 12 can be provided with a handle (not shown). As discussed further below, a computer system (not shown) is preferably in electrical communication with the POP spectrophotometer 10 for control thereof. It is contemplated that the housing assembly 12 can have an opening for receiving a universal serial bus (USB) cable to facilitate electrical communications and power to the POP spectrophotometer 10.

The chassis 16 of the housing assembly 12 is preferably formed integrally with the supports 18, though it is contemplated that the supports 18 and the chassis 16 can be provided otherwise. The chassis 16 includes a first side, which is referenced herein as a first chassis side 34, for receiving and mounting the optics and electronics. The chassis 16 further includes a second side, which is referenced herein as a second chassis side 36, and which is opposite the first chassis side 34 and facing a target plane $T_P$ along which a color sample may be positioned. Though reference is made herein to a "target plane" and a "target location," it shall be understand that the target location extends from the so-called "plane" so as to occupy a three dimensional space (see, e.g., depth "D" of FIG. 5).

The supports 18 can be provided as extensions or other elements for spacing the chassis 16 from the target plane $T_P$.

The supports 18 can be provided with a first end in secured relationship with the chassis 16, and a second end (or structure in association therewith) at least partially defining the target plane $T_P$. As shown, the supports 18 can be formed integrally with the chassis 16, such as by a metal casting or plastic molding, though it is contemplated that the secured relationship can be facilitated by fasteners and/or other suitable means known in the art.

The lid 20 cooperates with the chassis 16 to define a space in which the optics and electronics are contained. The lid 20 is preferably provided as a bonnet, and the chassis 16 can be provided with means for receiving the lid 20, such as a circumferential lip 38. A plurality of securing elements 22a, 22b can be provided to maintain the secure fit between the lid 20 and the chassis 16. For example, a first set of securing elements 22a can be longitudinally positioned at the top of the housing assembly 12 with pins 40 extending axially therefrom, and a second set of securing elements 22b can be provided at the sides of the housing assembly 12 to receive the pins 40, while fasteners are used to secure the securing elements 22b to the chassis 16 and/or supports 18 via threaded bores 42 formed therein, for example.

The chassis 16 is provided with a curved portion 44, which is preferably provided as a spherical or pseudo-spherical portion. The curved portion 44 is preferably positioned in the chassis 16 proximal a side thereof, so as to a further facilitate open viewing during operation of the POP spectrophotometer 10. It is preferable that the target location $T_L$ be visually-perceptible to a user during operation of the POP spectrophotometer 10, and a line of sight to the target location $T_L$ is made available to a user during operation of the POP spectrophotometer 10.

A plurality of mounts 46a-e are positioned at the curved portion 44. The mounts 46a-e are preferably formed integrally with the chassis and, more preferably, comprise receiving passages defined by a body portion of the chassis 16. Means for receiving and/or securing circuit boards 48, such as clips 50, are provided to be spaced-apart from the curved portion 44 and proximal the circumferential lip 38. Additional means for receiving and/or securing circuit boards can be provided with the housing assembly 12.

The mounts 46a-e are suitably sized, shaped, dimensioned, and otherwise configured to securingly position, respectively, the first illumination optical system 24a, the second illumination optical system 24b, the imaging optical system 26 (with or without targeting optical system 28), the sheen detection system 30, and the camera system 32. As shown, each one of the mounts 46a-e may include at least one generally cylindrical (and/or tiered) passage defined by the chassis 16. The chassis 16 is configured with corresponding openings through the second side 36, and each one of the systems 24a-32 has a line of sight to a target location TA through the second side 36 of the chassis 16 at one of the openings corresponding thereto (and such openings can be sealed with a transparent material to prevent contamination of the systems 24a-32). Springs and other suitable fastening devices can be provided in cooperation with the chassis 16 and/or mounts 46a-e thereof for removably mounting the systems 24a-32.

The housing assembly 12, including the chassis 16 and the supports 18, is preferably configured to mount the systems 24a-32 such that the lines of sight thereof are directed generally toward the target location $T_L$ of the target plane $T_P$. For example, the mounts 46a-e (and the length of the supports 18) are respectively configured to securingly position a plurality of the systems 24a-32 and/or lines of sight thereof as follows: (i) securingly position a first illumination line of sight $IL_{S1}$ of the first illumination optical system 24a toward the target location $T_L$ at substantially about forty-five degrees with respect to the target plane $T_P$; (ii) securingly position an imaging line of sight $IM_S$ of an imaging optical system 26 (with or without targeting optics) toward the target location $T_L$ and at substantially about ninety degrees with respect to the target plane $T_P$; (iii) securingly position a second illumination line of sight $IL_{S2}$ of the second illumination optical system 24b toward the target location $T_L$, at substantially about forty-five degrees with respect to the target plane $T_L$, and substantially about ninety degrees with respect to the first illumination line of sight $IL_{S1}$ as measured about the imaging line of sight $IM_S$; (iv) securingly position a line of sight $SH_S$ of a sheen detection system 30 toward the target location $T_L$, at substantially about forty five degrees with respect to the normal of the target plane $T_P$, and at substantially about ninety degrees with respect to the first illumination line of sight $IL_{S1}$ (or the second illumination line of sight $IL_{S2}$); and (v) position a camera line of sight $CA_S$ toward the target location $T_L$. In some aspects of the invention, the chassis 16 is configured to mount more or less systems and/or components than those described herein.

An alignment device 14 and/or other means can be provided for assisting a user of the POP spectrophotometer 10 in identifying the target location $T_L$. For example, an alignment device 14 can be provided in secure communication, preferably rigid, with the housing assembly 12. The alignment device 14 includes a plurality of protuberances 52 and a plurality of hinges 54 opposite thereto, and the protuberances 52 and hinges 54 cooperate with complementary fasteners (positive structure and/or negative space) provided with and/or defined by the housing assembly 12. The alignment device 14 includes a support plate 56 proximal the hinges 54, a plurality of rails 58 extending from the support plate 56, a plurality of frame elements 60 extending from the rails 58 opposite the support plate 56 and to the protuberances 52. The alignment device 14 depends from the second chassis side 36, and the rails 58, the support plate 56 and the frame elements 60 cooperate to define a central opening, which is referenced herein as an alignment aperture 62, and through which the lines of sight $IL_{S1}$, $IL_{S2}$, $SH_S$, $CA_S$, and $IM_S$ can pass to the target location $T_L$.

The alignment device 14 preferably includes a movable calibration plate assembly 64. The moveable calibration plate assembly 64 includes a plurality of overhang elements 66 depending from the rails 58, a calibration plate 68 extending between the overhang elements 66 and defining a central calibration surface 70, which is provided as a reflective white surface, and which is positioned at the center of the calibration plate. The central calibration surface 70 has an elevation aligned with a midpoint between (i) an elevation of the bottom surface of the lowest portion of the rails, and (ii) an elevation of the upper surface of the lowest portion of the rails. Thus, the alignment device 14 facilitates user-identification of the target location $T_L$, preferably without requiring adjustment or calibration because it is known to the user that target location $T_L$ is below the alignment aperture 62.

The distance from the central calibration surface 70 to the target plane is substantially about equal to depth D. It is contemplated that depth D can be about 0.215 inches, though other magnitudes are contemplated and can be determined in accordance with other characteristics, e.g., geometry of the POP spectrophotometer 10, tolerances of the systems 24a-32, etc.

The POP spectrophotometer 10 is preferably capable of measuring a color sample that has intrinsic variations in depth and/or a plurality of color samples that have variations in depth relative to each other. While facilitating identification of the target location $T_L$, the alignment device 14 can also be spaced apart from the target plane $T_P$ and the second chassis side 36 and/or systems 24a-32, such that the target plane $T_P$ and the alignment device 14 define a distance measurement, referenced herein as depth D, for the target location $T_L$. In this regard, when an environmental surface, such as a tabletop, is aligned with the target plane $T_P$, the alignment device 14 cooperates with the environmental surface to at least partially define the depth-variation of a color sample that can be utilized (e.g., depth D). The housing assembly 12 and the alignment device 14 are sized and dimensioned such that the depth D corresponds to that level of depth-insensitivity provided by the imaging optical system 26, the illumination optical system 24a (for example), and the corresponding electronics.

B. The Illumination and Imaging Optical Systems Generally

The POP spectrophotometer 10 includes at least one illumination optical system 24a, but may be provided with at least one additional illumination optical system, such as the second illumination optical system 24b. Illumination optical systems 24a, 24b are used to illuminate the target location $T_L$, by projecting light thereto. As further discussed below, the illuminated light is then reflected from the color sample, and travels, at least in part, toward the imaging optical system 26 (and optional systems 30 and 32). Discussion herein of illumination optical system 24a shall be understood to also apply to illumination optical system 24b unless stated otherwise. Certain typical components of illumination optics are known in the art and need not be discussed in detail herein.

Figure 10:
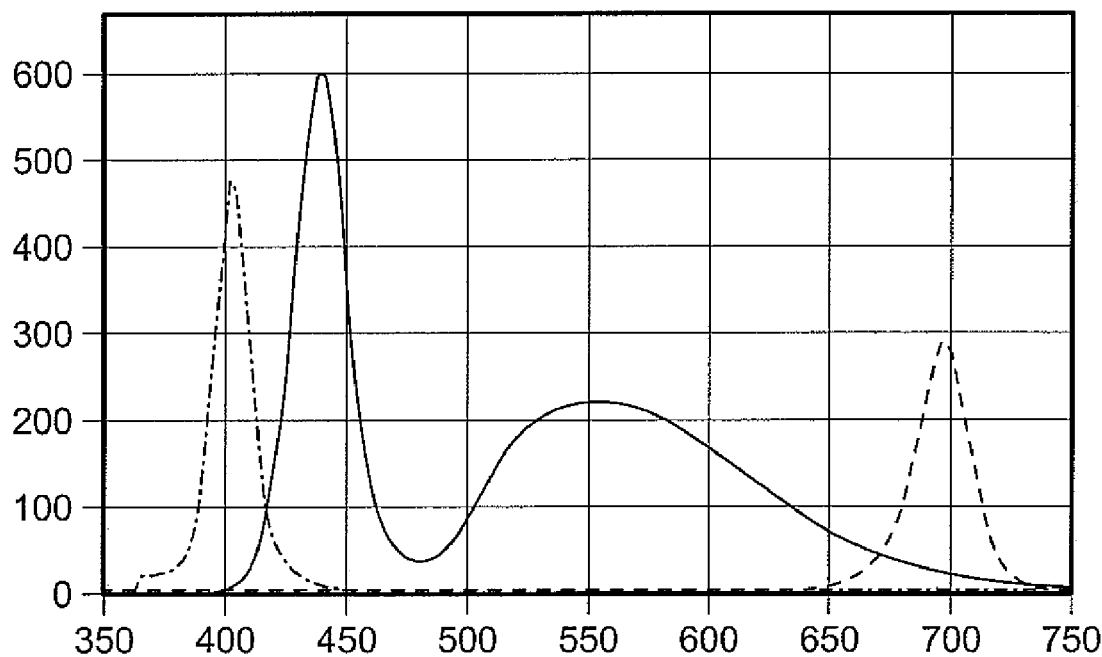
FIG. 10 is a table showing the distribution of light energy across the visible spectrum for the LED cocktail of the general type shown in FIGS. 9 and 10.
Figure 11:
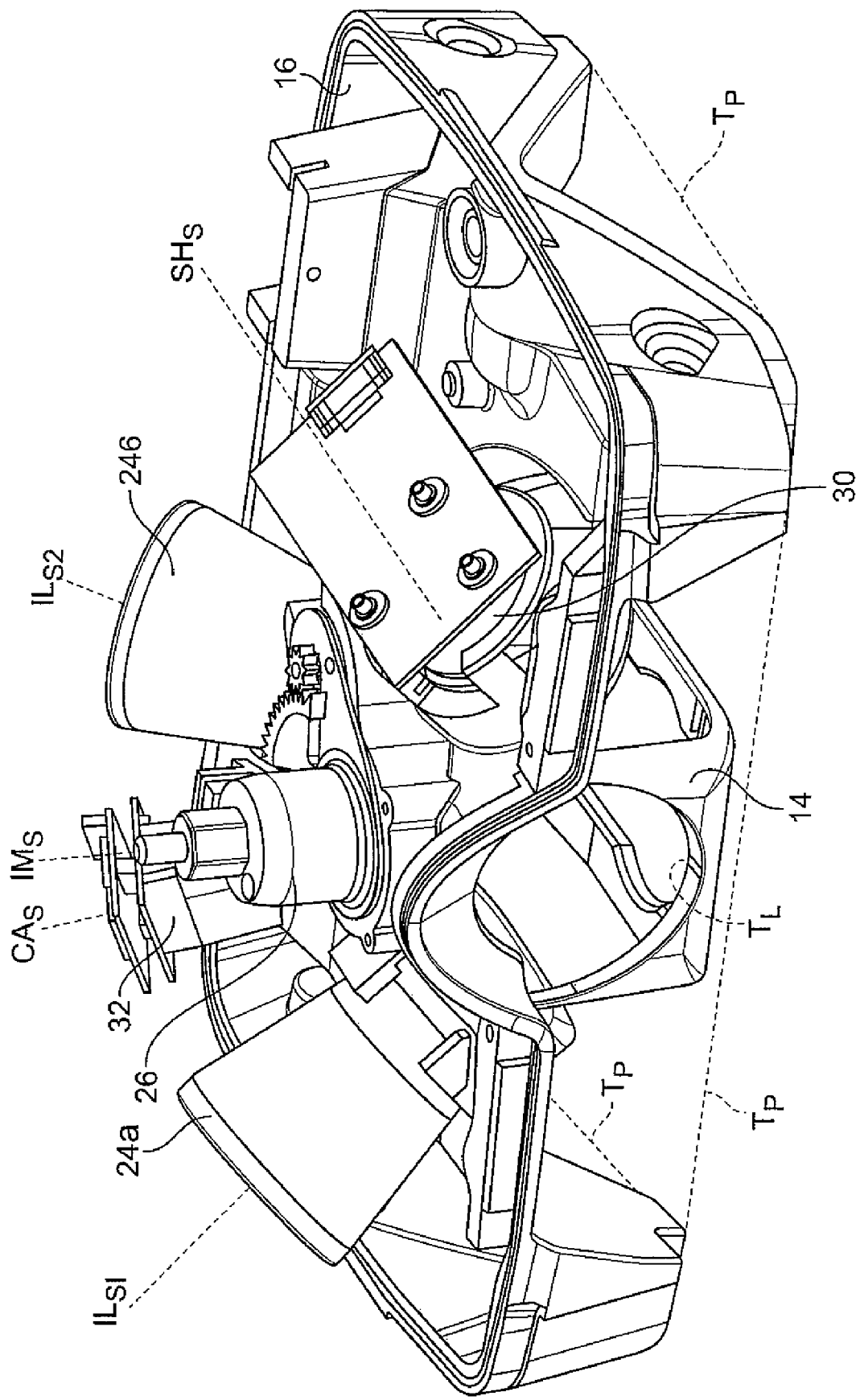
FIG. 11 is a front perspective view of a second partial assembly that includes the first partial assembly of FIG. 7 and that further includes an imaging optical system having a targeting optical system.

Optical assemblies for illuminating a color sample are known in the art, and any suitable optical assembly for illumination can be used. However, it is preferable for such optical assembly to include a plurality of LEDs. In this regard, illumination optical systems 24a, 24b are each provided with an LED cocktail 72. The LED cocktail 72 can include for example, a white LED 74, and a plurality of chromatic dies, such as two deep red LEDs 76 and three deep blue LEDs 78 or dies. Reference is made to FIG. 10, which shows a sample distribution of light energy across the visible spectrum for an LED cocktail of the general type shown in FIGS. 9 and 10.

The LED cocktail 72 is provided as a full spectrum LED (hybrid of white die plus supplemental chromatic die) illumination source that provides high reliability over a long life. The hybrid LED cocktail 72 utilizes a high power white LED 74 with supplemental chromatic dies 76, 78 to achieve a full spectrum white light (about 390 nanometers to about 710 nanometers) that has optical energy across substantially the entire visible spectrum. The white die and chromatic die used to supplement the spectrum are arranged in a tightly clustered package that provides a small illumination source diameter to approximate, as much as possible, a point source for the searchlight illumination optics of the illumination optical systems 24a, 24b. The LED cocktail 72 also provides a common substrate with very high thermal conductivity, an on substrate heating source, and a sensing thermistor to precisely manage die temperature. Thermal stabilization is further discussed below.

Figure 12:
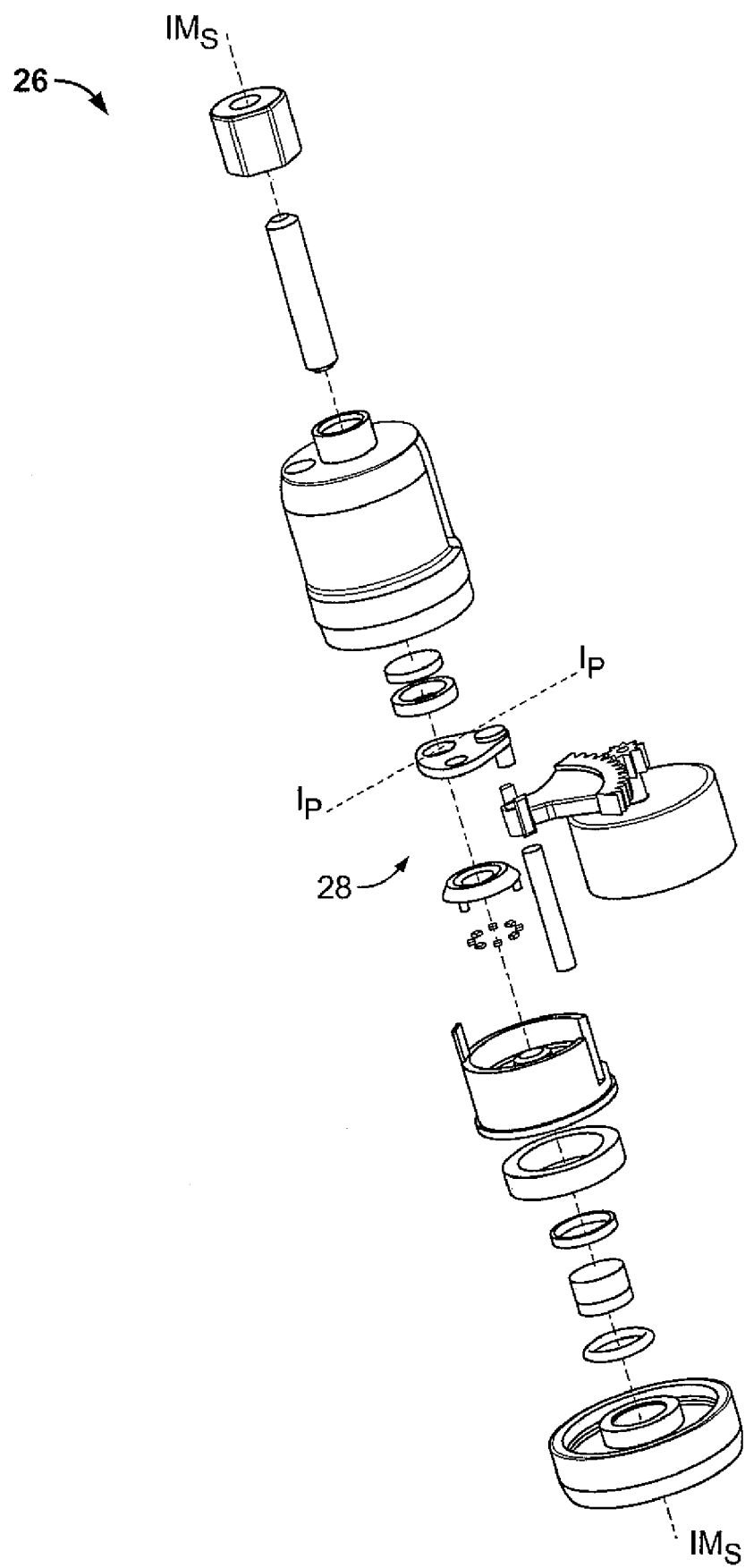
FIG. 12 is a schematic showing a sample of the imaging optical system with the targeting optical system of FIG. 11.

The POP spectrophotometer 10 further includes an imaging optical system, such as that shown in FIG. 12 (an imaging optical system 26 including a targeting optical system 28). Optical systems for imaging of the prior art may also suffice, in some embodiments. Optical systems for imaging are known in the art and are used to perceive illuminated light reflected from a sample for color measurement thereof according to known techniques. Moreover, the spectrophotometer can include any means for measurement and communication of the sensed image. For example, a 31-channel color wheel can be provided in cooperation with a photodiode on one of the circuit boards, such that collected light can pass from a fiber optic through a spectral band pass filter on a wheel and onto a photodiode for color measurement. Addition structure can be provided for mounting same (see, e.g., FIG. 14). Similarly, suitable electronics are known in the art for controlling this process and can be included in the POP spectrophotometer 10.

Disclosed herein is an optional targeting optical system 28, which can be positioned inline with and/or as part of an imaging optical system 26. Such targeting optical system 28 shall be further discussed below after further discussion of some of the features provided by cooperation between the imaging optical system 26 and the illumination optical systems 28.

C. Ambient Light Insensitivity & Defeating Interference Synchronous Modulation-Demodulation and Active Thermal Stabilization The illumination optical systems 24a, 24b can cooperate with the imaging optical system 26 and associated electronics to implement a synchronous modulation-demodulation scheme (SMD scheme) for providing comprehensive ambient light immunity and to facilitate open-viewing of the color sample during measurement. Utilization of an SMD scheme modulates the light projected by the LED cocktails 72 of illumination optical system 24a, 24b to a frequency distinct from and greater than that of common sources of ambient light, and, when the light is reflected from the color sample and detected by the imaging optical system 26, such light is synchronously demodulated from such frequency for measurement of the color of the color sample. Because the spectral and spatial emission characteristics of the LED can vary in response to small changes in temperature, it is preferable for the illumination optical systems 24a, 24b to incorporate on-substrate active thermal stabilization to control variance in temperature, thereby inhibiting undesirable types of temperature-induced variation. LED drive electronics provide high frequency modulation that is synchronized with the detection electronics to provide detection ands amplification that has high noise immunity to both electrical noise and optical (i.e. ambient light) noise.

Various SMD schemes are known in the art, and reference is made to commonly-owned U.S. Pat. No. 6,883,633. However any suitable optics and/or electronics can be incorporated for defeating interference and ambient light. It is preferred for such optics and/or electronics to incorporate the following qualities: (i) the technique used preferably renders the POP spectrophotometer 10 insensitive to a wide range of ambient light sources and intensities, some of which (such as sunlight) may be many times "brighter" than the illumination optical systems 24a, 24b; (ii) application of the technique for minimizing sensitivity to ambient light preferably occurs before or at the initial stage of signal processing so that the dynamic range and signal to noise margins of the associated electronics are predictable and maintained; and (iii) techniques applied for minimizing sensitivity to ambient light preferably differentiate between characteristics of ambient light and those of the illumination optical systems 24a, 24b in the frequency domain.

Since modern architectural illumination technology may have multi-frequency artifacts, the frequency of operation for the illumination optical systems 24a, 24b is to be differentiated from that present in ambient light. This can be accomplished by "pushing" the illumination frequency of operation higher than those artifacts typically found in ambient light and by providing associated electronics for rejecting those artifacts in close proximity to the illumination frequency of operation. It is contemplated that the frequency of operation can be adjustable, such as to account for possible future variations in commonplace ambient light characteristics. In this regard, potential conflict between the frequency of operation and ambient light artifacts can be minimized.

In some embodiments, it is contemplated that insensitivity to ambient light can be achieved with "brute force" through the use of a xenon flash or a similarly bright light source during the measurement.

D. Depth-Insensitivity & Defeating the Inverse Square Law Over-Illumination and Spatially-Compensated Optics The illumination optical systems 24a, 24b can cooperate with the imaging optical system 26 and associated electronics to implement a depth-insensitivity for defeating the inverse-square law. The POP spectrophotometer 10, in some embodiments, provides searchlight illumination optics in combination with image based spatially compensated collection optics to achieve a systemic optical depth insensitivity over an extended range. The POP spectrophotometer 10 provides for depth of field insensitivity through careful consideration of both the illumination optical systems 24a, 24b and the imaging optical system 26 relative to the target plane $T_P$. Briefly, the Inverse Square Law, which is known in the art, relates to the proposition that the intensity of reflected light is diminished as the distance of the color sample from the illumination source increases.

The POP spectrophotometer 10 minimizes errors associated with the Inverse Square Law by firstly deploying multiple "searchlight" illumination beams whose 'apparent' source is at infinity, thus generating a sufficient volume in the space where the beams intersect that over-illuminates the target location $T_L$ with uniform light that contains virtually no significant effect from the Inverse Square Law. The illumination optical system 24a is provided so as to over-illuminate the target location $T_L$. Because varying color samples reflect the illuminated light in varying directions, more than one illumination optical system is preferable, so as to enhance the amount of light reflected toward the optics of the spectrophotometer, such as the imaging optical system 26, sheen detection system 30, and camera system 32. In this regard, it is contemplated that any number of illumination optical systems can be provided in some aspects of the present invention.

In some embodiments, the illumination optical systems 24a, 24b incorporate the smallest possible full spectrum LED light source with a two element collimator design to provide for constant irradiance on the target plane $T_P$ through depth of field. It is preferred to incorporate at least two illumination optical systems 24a, 24b to illuminate the target plane $T_P$ at forty-five degrees to sample normal. The two illumination optical systems 24a, 24b are in turn angularly displaced at about ninety degrees from each other around the target (sample) normal. In this regard, the target plane $T_P$ is over-illuminated enough to provide constant target (sample) area irradiance in the overlapped region as the sample is moved the instrument's prescribed depth of field (DOF).

Figure 13:
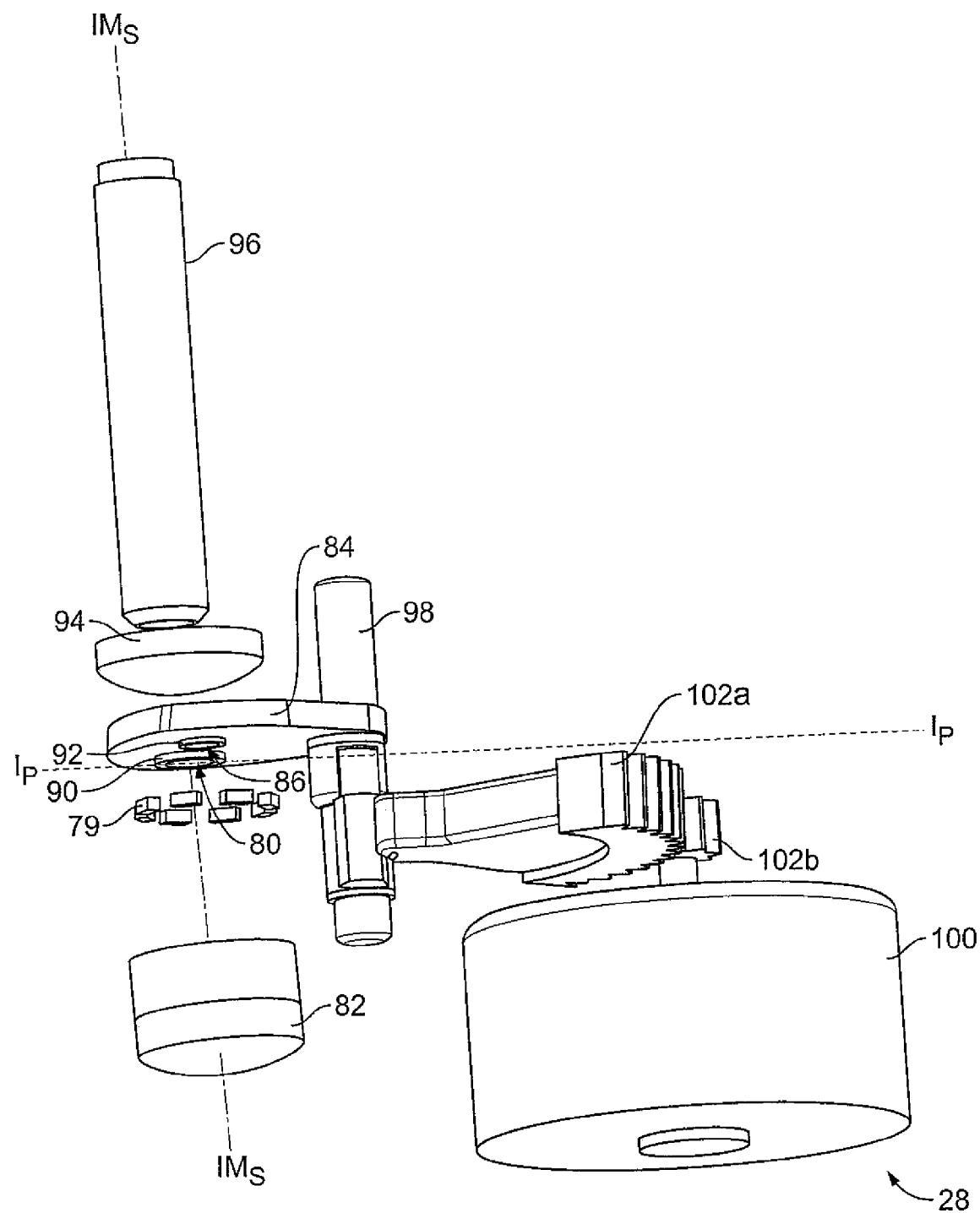
FIG. 13 is a schematic showing the targeting optical system of FIGS. 11 and 12.
Figure 14:
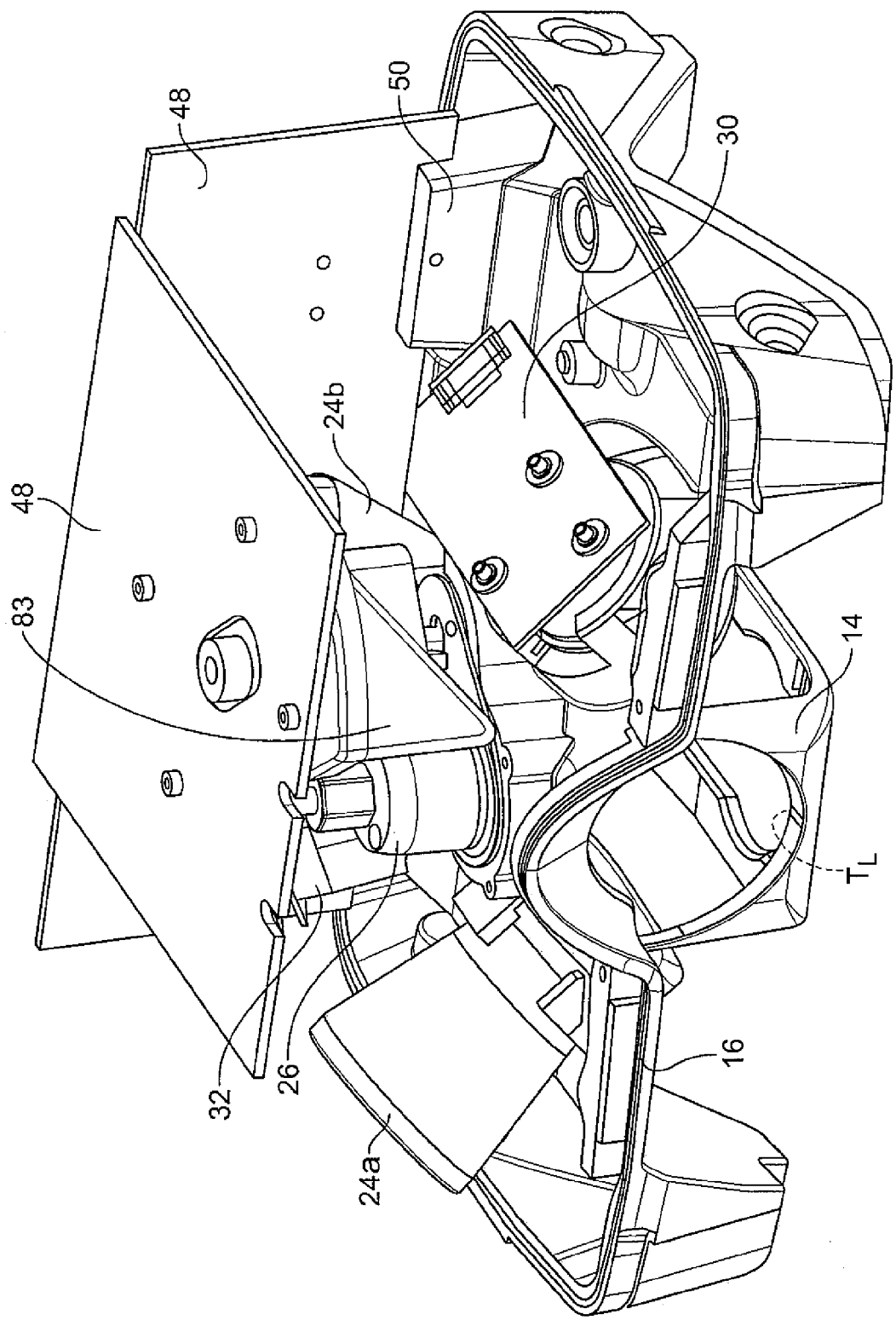
FIG. 14 is a front perspective view of a third partial assembly that includes the second partial assembly of FIG. 11 and that further includes a plurality of circuit boards.
Figure 15:
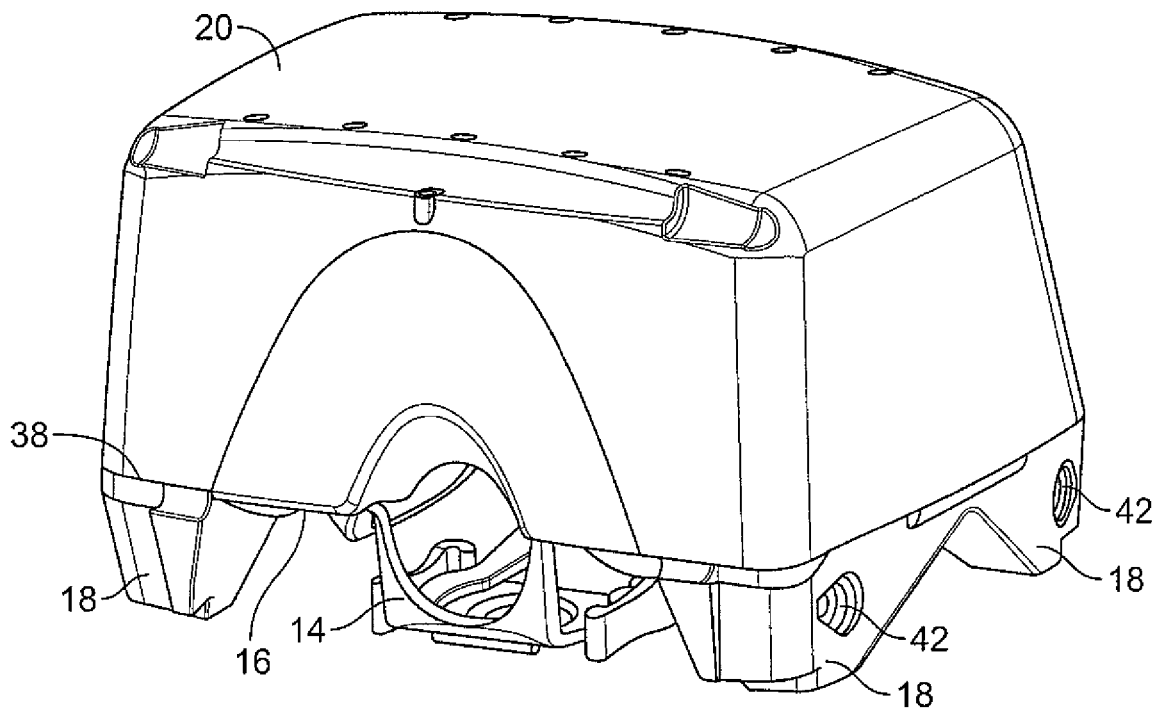
FIG. 15 is a front perspective view of a fourth partial assembly that includes the third partial assembly of FIG. 14 and that further includes a lid abutting the chassis.
Figure 16:
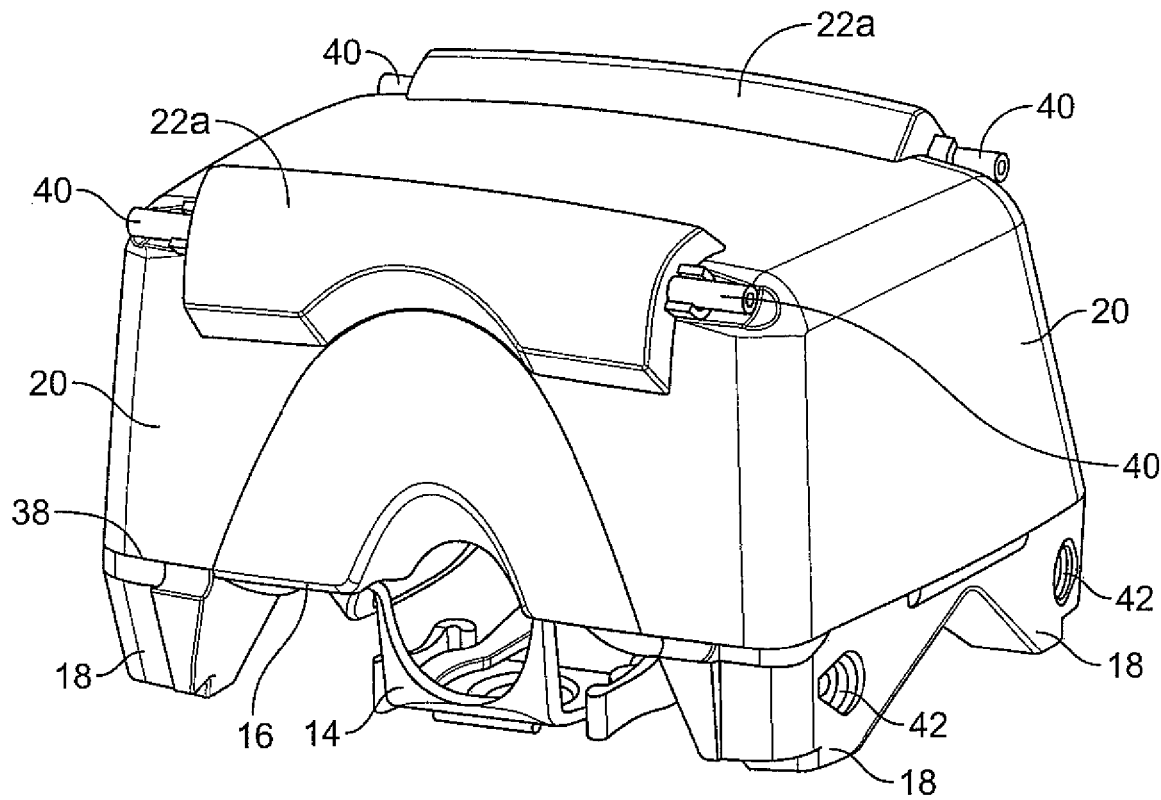
FIG. 16 is a front perspective view of a fifth partial assembly that includes the fourth partial assembly of FIG. 15 and that further includes a first set of securing elements for securing the lid to the chassis.

Secondly, this illumination technique cooperates with a sensor 82 in the imaging optical system 26, whose light collection optics is image-based and spatially compensated with respect to the target location $T_L$ of the color sample. As shown in FIG. 13, at least one aperture 80 placed at the image plane $I_P$ of the collector optic, just upstream of the sensor 82, allows the sensed area of the color sample to grow with the square of distance and thereby optically nullify the inverse square effect of the light traveling from the target location $T_L$ to the sensor 82.

In some embodiments, the aperture 80 located at the image plane $I_P$ also provides means for high target selectivity assuring a strong and uniform sensitivity to the target location $T_L$ of the target plane $T_P$. (As will be further discussed below, a switchable aperture assembly 84 can be provided that has at least a second aperture 86 in addition to the first aperture 80, wherein each of the apertures 80, 86 is switchable alignable with the imaging line of sight $IM_S$.)

Thus, in addition to controlling the illumination uniformity, imaging of the sample area onto the image plane $I_P$ provides a natural compensation for the Inverse Square Law effect of object distance. The Inverse Square Law that governs the scattered irradiance reflected from each unit area within the target spot is compensated by the "viewed area" of the imaging system that varies with the square of the distance thereby canceling or nullifying a physical effect that generally renders depth variation as intolerable. The effectiveness of depth insensitivity is governed by a plurality of interrelated variables, including (i) the angular geometry between the illumination lines of sight $IL_{S1}$, $IL_{S2}$ and the imaging line of sight $IM_S$ (which determines how much the measured spot moves within the illuminated spot as a function of distance); (ii) by the relative spot sizes of over-illumination spot vs. measured spot that determines the "travel zone" within which the measured spot can wander; and (iii) the focal "depth of field" offered by the imaging optical system 26 (e.g., distance D of FIG. 5). The depth of field of the imaging optical system 26 is preferably large enough to provide an acceptable level of target selectivity over the depth of field.

Though instrument measurement error due to depth variation and the Inverse Square Law can be eliminated optically, an alternate or additional system might (i) allow "measurement error" due to the Inverse Square Law acting upon distance variation, and (ii) correct the measurement error mathematically (e.g., by utilizing an accurate input indicating the degree of distance variation).

E. The Targeting Optical System

In some embodiments of the present invention, the POP spectrophotometer 10 includes a targeting optical system 28, and, it is preferable for the targeting optical system 28 to be included as a subsystem of the imaging optical system 26 and inline with the imaging line of sight $IM_S$. In this regard, in some aspects of the present invention, the selected aperture can be used to both (i) define the perceived target size for measurement, and (ii) visually identify to the user the circumference of the target location at which the sample is to be positioned. As indicated above, it is preferable for the user to have a line-of-sight to the target location $T_L$ during operation of the POP spectrophotometer, and it is contemplated that the targeting optical system 28 further identifies the target location $T_L$ to the user.

Multiple sample target sizes are possible by means of a switchable aperture assembly 84 located at the image plane $I_P$ of the imaging optical system 26. An LED targeting ring 79 circumscribes the imaging line of sight $IM_S$ and is positioned between the sensor 82 and switchable aperture assembly 84. The switchable aperture assembly 84 includes a plate 88, a first aperture 80, a first reflective ring 90 circumscribing the first aperture 80 and having a size, e.g., radius corresponding to that of the first aperture 80, a second aperture 86, and a second reflective ring 92 circumscribing the second aperture 86 and having a size, e.g., radius corresponding to that of the second aperture 86. It is contemplated that the plate 88 can include additional apertures and additional reflective rings associated therewith. The apertures 80, 86 each function as a field stop that define the area over which color information is collected at lens 94 and communicated to fiber optic 96. At the same time, the reflective rings 90, 92 provide a reflective surface for an active targeting system, e.g., they reflect light from the LED targeting ring 79 and project same toward the target location $T_L$ to facilitate user identification thereof. The switchable aperture assembly 84 can be moved between a plurality of positions by any means known in art. For example, the switchable aperture assembly 84 can be provided with a shaft 98 secured thereto, a motor 100, and a plurality of gears 102a, 102b in mechanical communication with the shaft 98 and the motor 100 to facilitate communication of a driving force. Suitable electronics are provided for controlling the motor 100 and intermediating control signals/commands from the computer system.

The use of active targeting via a projected light ring facilitates accurate identification of the area to be measured. The retro-illumination technique disclosed herein further enhance accuracy when the targeting optical system 28 is included as part of the imaging optical system 26, because the projected LED targeting ring 79 remains in alignment with the target location $T_L$. The "active targeting" changes size right along with the selected one of the apertures 80, 86 when switching between the large or measurement small spot size. Moreover, in some embodiments, use of switchable apertures allows for large or spot measurements without requiring a user to stop and mechanically recalibrate the POP spectrophotometer 10.

During a targeting/alignment phase of a the measurement cycle, the selected one of the apertures 80, 86 is illuminated by the LED targeting ring 79. One of the reflective rings 90, 92 surrounding the selected one of the apertures 80, 86 projects a targeting ring of light through the sensor 82 that shines on the color sample to define the target location $T_L$ and facilitate user-identification thereof. The switchable aperture assembly 84 enables a user to change the aperture size at the image plane $I_P$, which allows for a single imaging optical system that allows multiple measurement spot sizes utilizing the same optics, while providing effective means to provide active targeting thru retro-illumination thru the same optic to clearly and accurately identify to the user the exact area, e.g., the target location $T_L$, that will be measured. It is contemplated, for example, that the multiple spot diameter sizes can be six millimeters, twelve millimeters, and/or any other suitable diameter. Such techniques enhance very high spatial selectivity of targeted vs. non-targeted area.

F. The Sheen Detection System

The POP spectrophotometer 10 can be provided with a sheen detection system 30 for enhancing measurement of the color sample. Though the sheen detection system 30 is "optional" (as may also be the mount 46d therefor), it is preferable in the retail context to provide the sheen detection system 30, so as to satisfy the rising expectations of the retail market by further enhancing the quality of color matches to the color sample.

Suitable sheen detection systems are known in the art. However, in the POP spectrophotometer 10, it is preferable to position a sheen detection system 30 at a particular geometry relative to at least one of the illumination optical systems 26a, 26b. The sheen detection system 30, as well as the optical sensor and line of sight $SH_S$ thereof, is preferably provided to intercept and measure the specular reflections from the target location $T_L$ that originate with at least one of the forty-five degree illumination sources, e.g., with the first illumination optical system 24a, the second illumination optical system 24b, etc. The sheen detection system 30 is preferably equipped with a radiometer that collects the specularly reflected light from the sample surface during a measurement. In some embodiments, the sheen detection system 30 can be characterized as a gloss sensor assembly and can include an imaging lens, a spectral filter, and a photocell. The sheen detection system 30 is aimed at about forty-five degrees from the nominal sample plane, e.g., the target plane $T_P$, in a location that is at a ninety degree angle (coplanar) with respect to one of the illumination optical systems 24a, 24b that are preferably positioned as a searchlight and at forty-five degrees with respect to the target plane $T_P$. An image of the white LED 74 from said co-planar one of the illuminator optical systems 24a, 24b is formed on a high dynamic range photodiode located at an image plane of the radiometer. The spectral response of the sheen detection system 30 is matched to that of the CIE standard photometric observer using specially formulated color filters placed in the optical path, such as those filters of the color wheel discussed above. Field selectivity for the specularly reflect light at the sheen detection system 30 is provided as an internal aperture that defines a circular sample area within the test region defined by the projected targeting ring.

The sheen level of a test sample is automatically measured and matched for a customer during a normal color measurement cycle. This sheen data is then used to select the paint base with the closest sheen level to the sheen of the customer provided sample. A forty-five degree gloss level calculation is then algorithmically processed in connection with the associated electronics and/or the computer system to correlate to independently measured sheen levels of the paint bases being served by the formulation system to thereby allow accurate and automatic sheen detection, paint base selection with correct sheen, and/or cross sheen compensation. The sheen data can of course be ignored if the desired sheen level has already been pre-determined.

Thus, in embodiments of the invention incorporating the sheen detection system 30, the POP spectrophotometer 10 can detect the relative gloss of a customer's color sample during color measurement to automatically select the paint base with correct sheen level, e.g., Flat, Eggshell, Satin, Semi-gloss, etc. Moreover, the associated electronics and/or computer system can be provided with means for color correcting paint formulation when matching to a different level of sheen.

G. The Camera System

The imaging optical system 26 (with or without the active targeting of the optical system 28) can be optionally supplemented by a camera system 32 for camera-based imaging. Suitable computer code (hardwired, software, etc.) can be provided in connection with camera system for controlling same. Camera-based imaging is known in the art, though the camera system 32 can be provided so as to created numerous synergies.

For example, an optional camera system 32 (and optional mount therefore 46e) can be provided to facilitate creation of a permanent data record of the orientation of the color sample that existed prior to measurement thereof. This is particularly of interest if the color sample is not a solid color but a print or pattern of the type that cannot typically be re-measured accurately without such a record. As another example, should the POP spectrophotometer 10 be placed on an environmental surface, e.g., desk surface, that is "uneven" to such a degree so as to cause error in optically defeating the Inverse Square Law with the systems 24, 24b, 26 and/or reducing tilt errors, image data from the camera-based imaging of the camera system 32 can be evaluated algorithmically in combination with the data of the imaging optical system 26 to provide a more accurate measurement than what might have occurred without the camera system 32.

H. Electronics and Communications

In general, it will be apparent to one of ordinary skill in the art that some of the embodiments as described hereinabove may be implemented in many different embodiments of software, firmware, and/or hardware. The software code or specialized control hardware used to implement some of the present embodiments is not limiting of the present invention. For example, the embodiments described hereinabove may be implemented in computer software using any suitable computer software language type such as, for example, C or C++ using, for example, conventional or object-oriented techniques. Such software may be stored on any type of suitable computer-readable medium or media such as, for example, a magnetic or optical storage medium. Thus, the operation and behavior of the embodiments are described without specific reference to the actual software code or specialized hardware components. The absence of such specific references is feasible because it is clearly understood that artisans of ordinary skill would be able to design software and control hardware to implement the embodiments of the present invention based on the description herein with only a reasonable effort and without undue experimentation.

Moreover, the processes associated with the present embodiments may be executed by programmable equipment, such as computers. Software that may cause programmable equipment to execute the processes may be stored in any storage device, such as, for example, a computer system (non-volatile) memory, an optical disk, magnetic tape, or magnetic disk. Furthermore, some of the processes may be programmed when the computer system is manufactured or via a computer-readable medium. Such a medium may include any of the forms listed above with respect to storage devices and may further include, for example, a carrier wave modulated, or otherwise manipulated, to convey instructions that may be read, demodulated/decoded and executed by a computer.

It can also be appreciated that certain process aspects described herein may be performed using instructions stored on a computer-readable medium or media that direct a computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary. A computer-readable medium may further involve one or more data signals transmitted on one or more carrier waves.

A "computer" or "computer system" may be, for example, a wireless or wire line variety of a microcomputer, minicomputer, server, mainframe, laptop, personal data assistant (PDA), wireless e-mail device (e.g., "Blackberry" trade-designated devices), cellular phone, cable box, pager, processor, fax machine, scanner, or any other programmable device configured to transmit and receive data over a network. Computer devices disclosed herein may include memory for storing certain software applications used in obtaining, processing and communicating data. It can be appreciated that such memory may be internal or external to the disclosed embodiments. The memory may also include any means for storing software, including a hard disk, an optical disk, floppy disk, ROM (read only memory), RAM (random access memory), PROM (programmable ROM), EEPROM (electrically erasable PROM), and other computer-readable media.

I. Embodiments of the POP Spectrophotometer

In various embodiments of the present invention disclosed herein, a single component may be replaced by multiple components, and multiple components may be replaced by a single component, to perform a given function or functions. Except where such substitution would not be operative to practice embodiments of the present invention, such substitution is within the scope of the present invention.

Figure 1B:
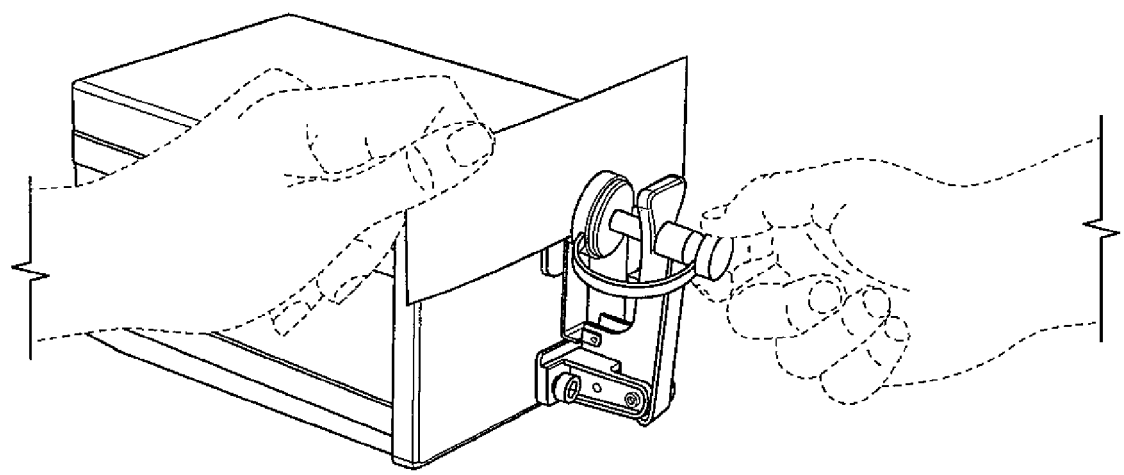
FIG. 1B is a perspective view of the prior art POP spectrophotometer of FIG. 1A together with a color sample and the stop shown in a second position.
Figure 2:
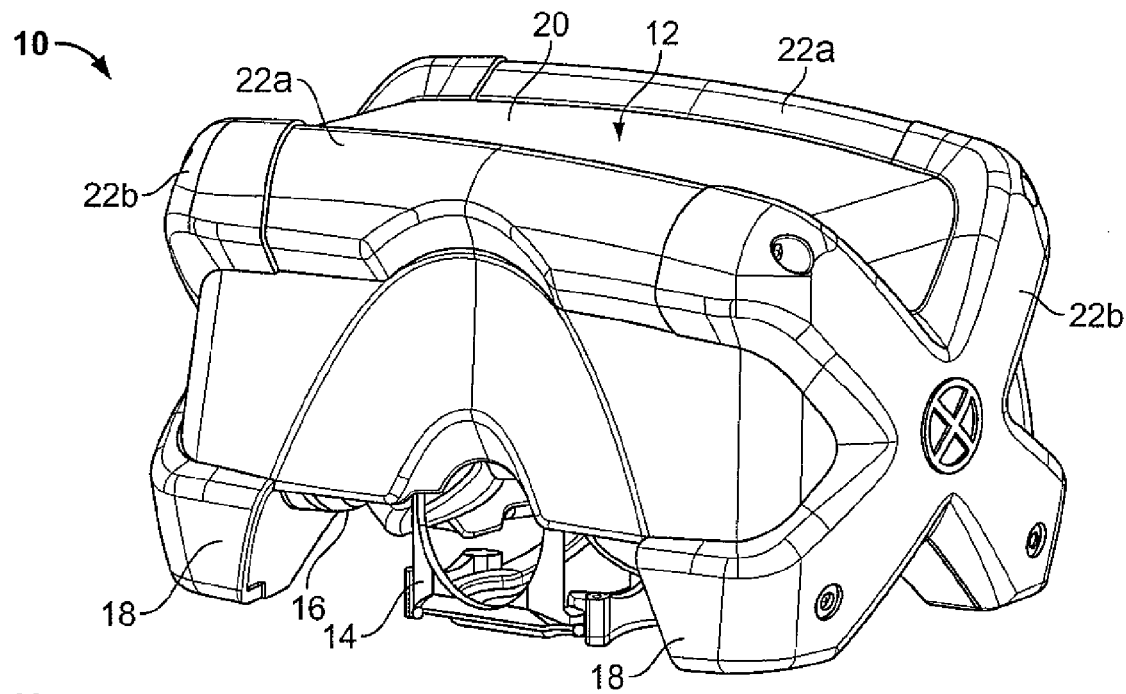
FIG. 2 is a front perspective view of a POP spectrophotometer constructed in accordance with an exemplary embodiment of the present invention, the POP spectrophotometer including an alignment device in a first or "calibration" position and further including a housing assembly that includes a chassis with a plurality of supports integrally formed therewith, a lid, and a plurality of securing elements securing the lid to the chassis.
Figure 3:
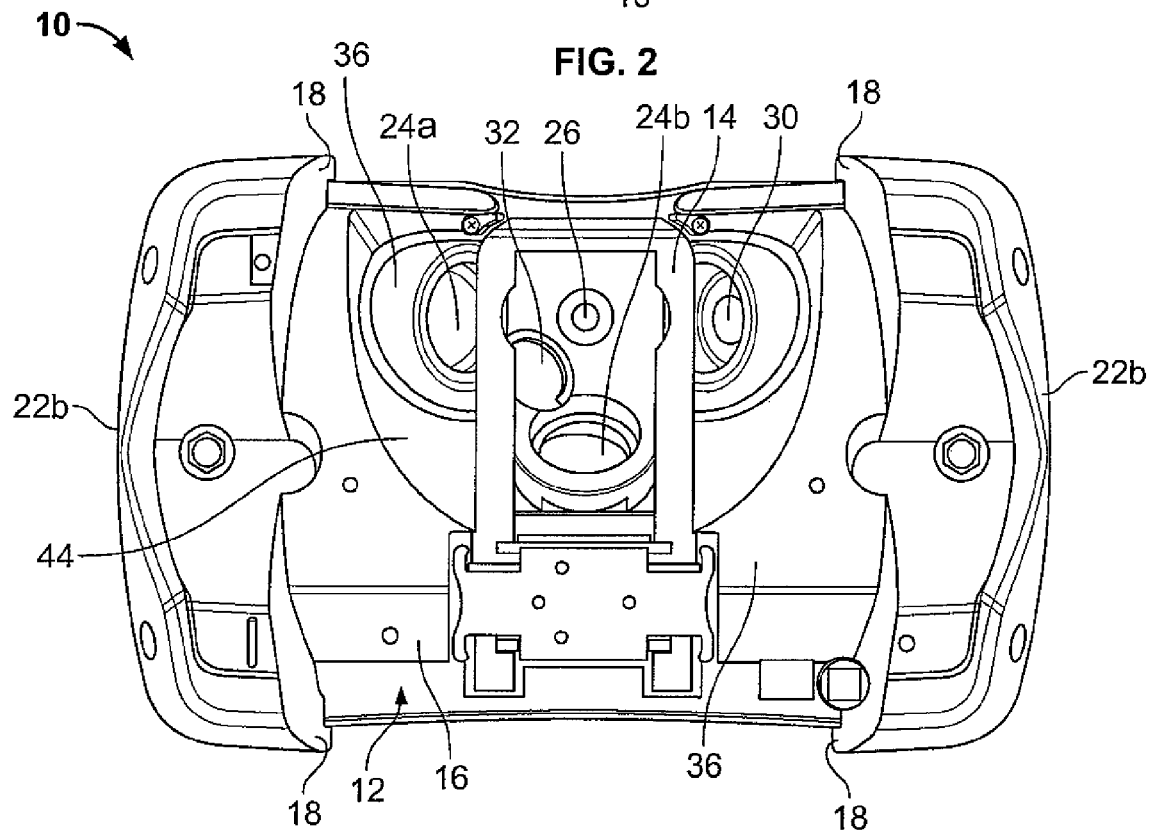
FIG. 3 is a bottom plan view of the POP spectrophotometer of FIG. 2 with the alignment device being shown in a second or "viewing" position.
Figure 4:
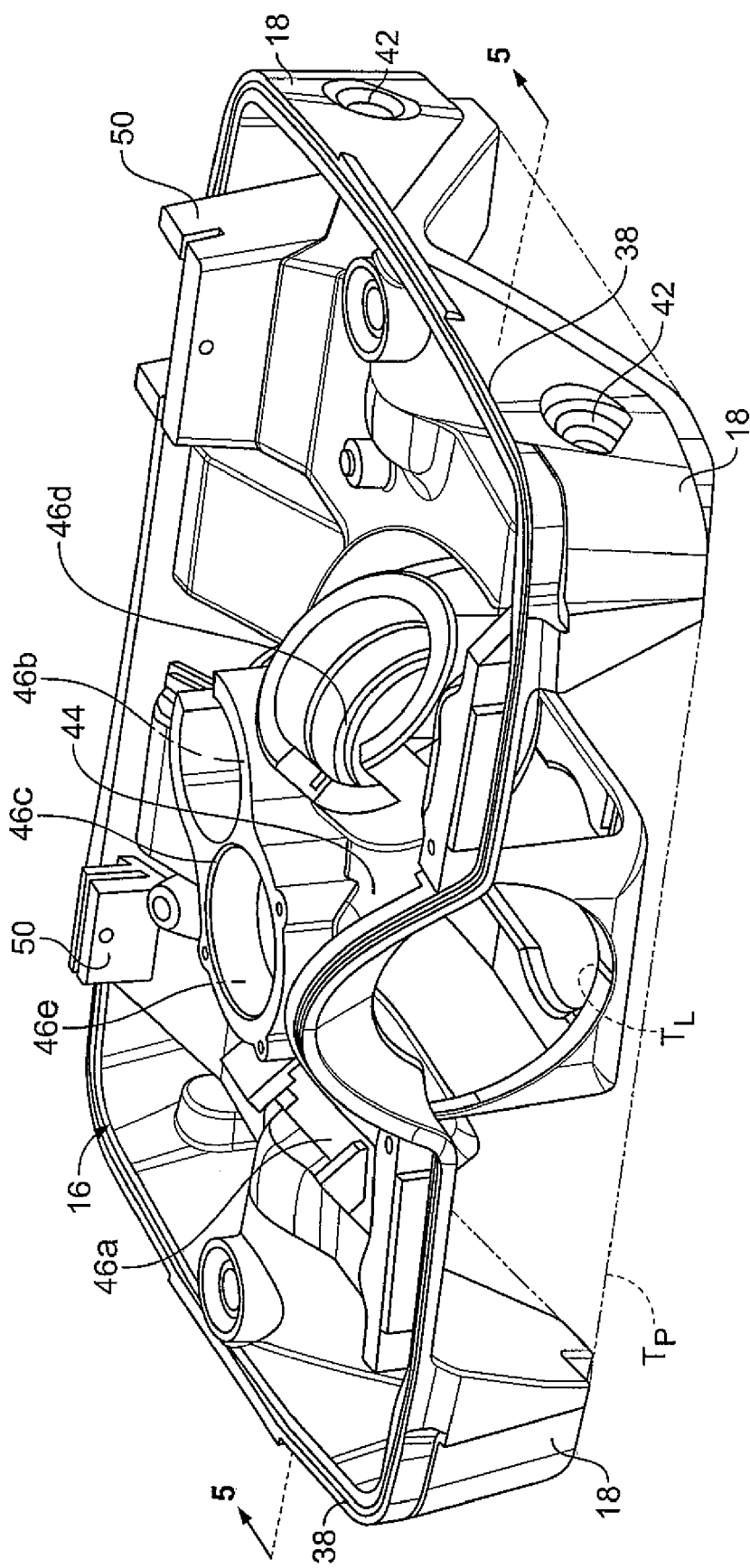
FIG. 4 is a front perspective view of the chassis with supports of the POP spectrophotometer of FIGS. 2 and 3.
Figure 5:
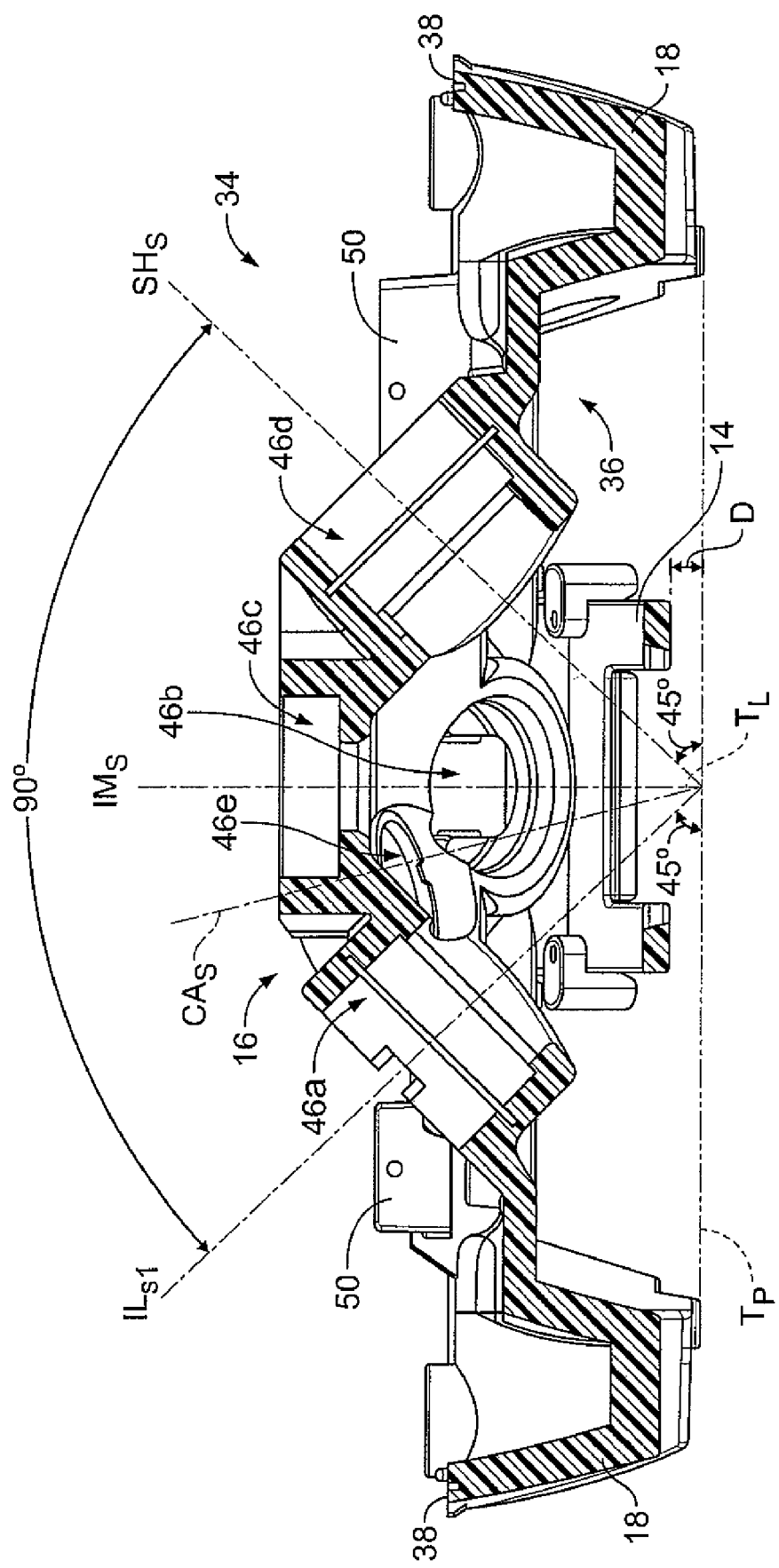
FIG. 5 is a sectional view of the chassis with supports taken along section line 5-5 of FIG. 4.
Figure 7:
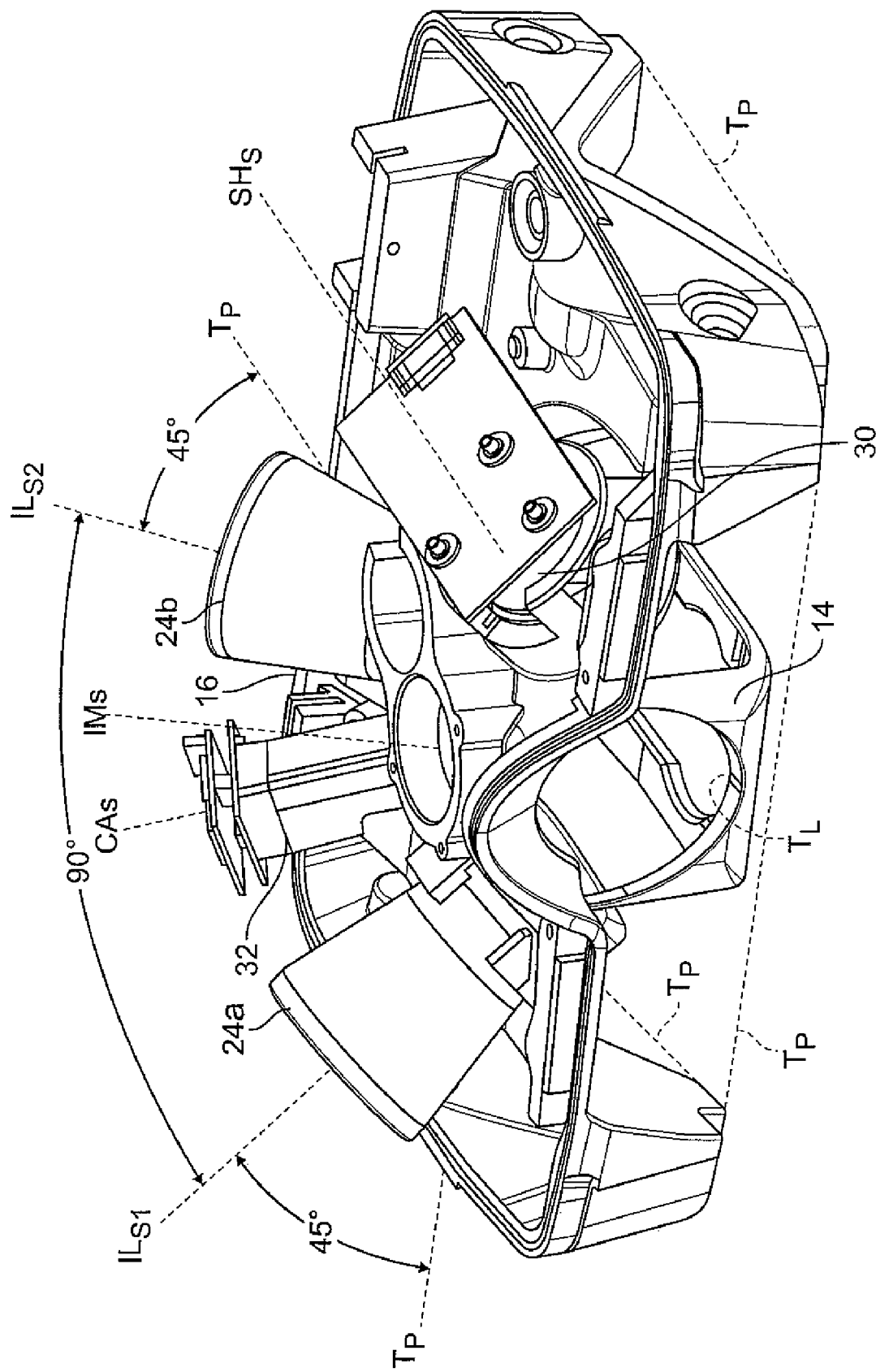
FIG. 7 is a front perspective view of a first partial assembly that includes the chassis with supports of FIG. 4 and that further includes a plurality of illumination optical systems, a camera system, and a sheen detection system.
Figure 8:
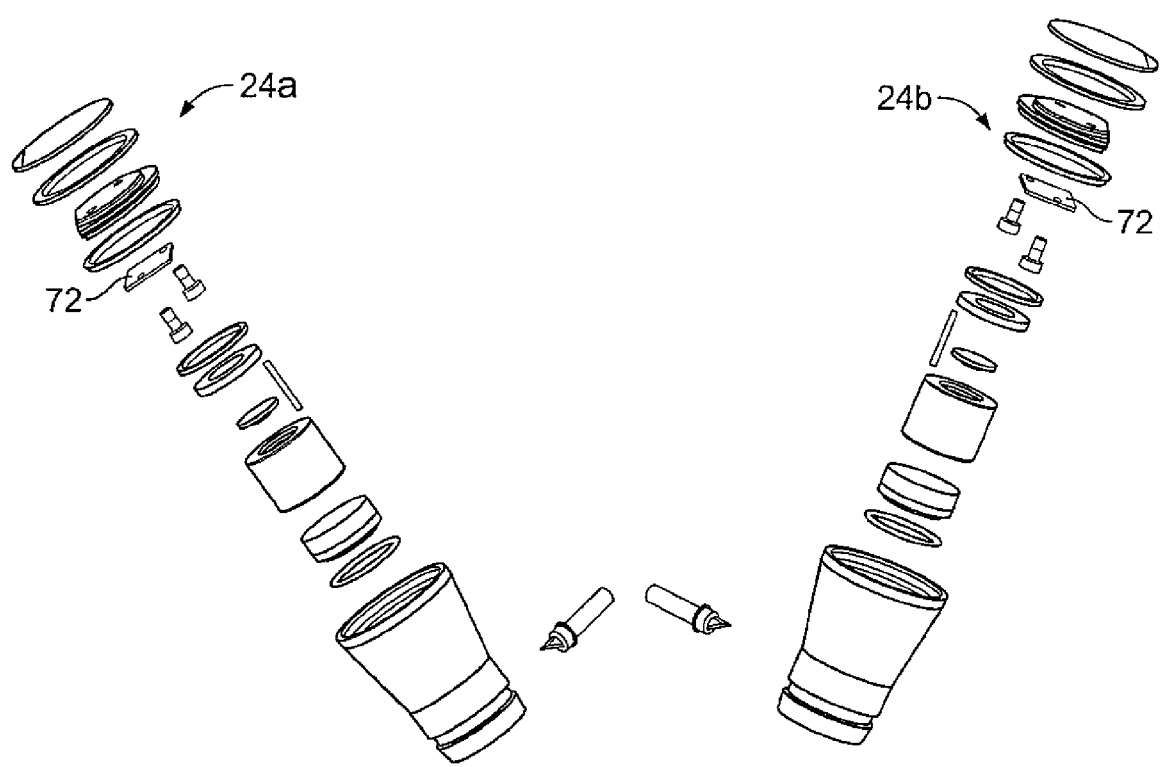
FIG. 8 is a schematic showing the illumination optical systems of FIG. 7, each being shown to include an LED cocktail.
Figure 9:
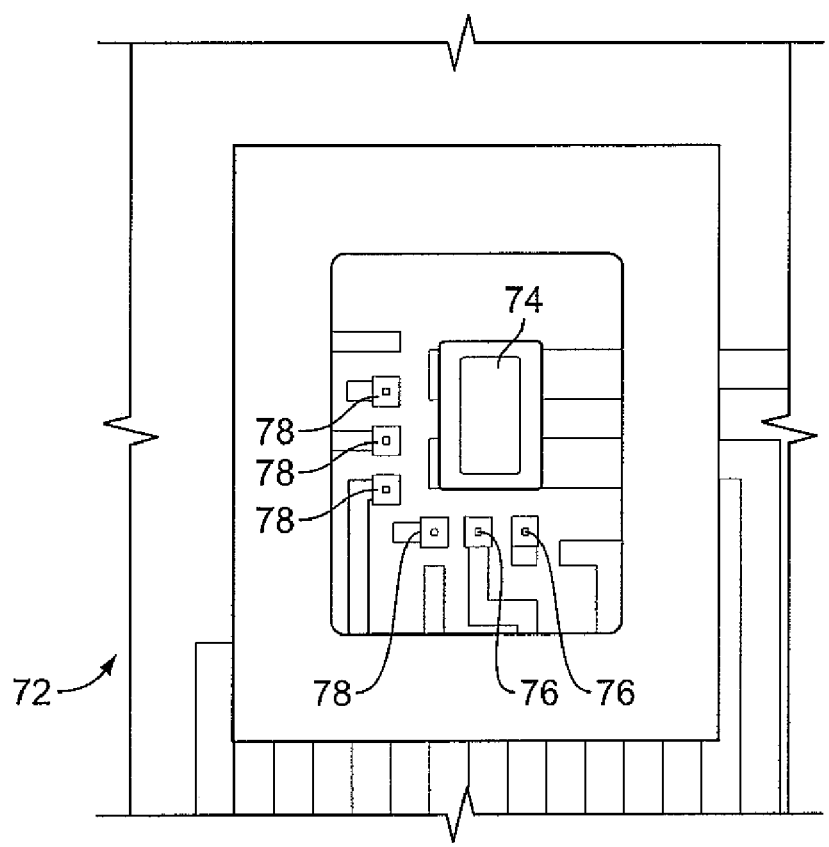
FIG. 9 is a schematic showing one of the LED cocktails of FIG. 8.

Preferred embodiments of the present invention provide numerous advantages. For example, preferred embodiments of the present invention do not mandate inclusion of a pivoted sample holder, such as that shown in FIGS. 1A-1B, but allow a user, such as a consumer, to easily position a color sample with one hand. In some aspects, preferred embodiments of the present invention can facilitate the following advantages:

Ability to easily recognize, select, and/or align the area of the color sample to be measured;

Ability to easily select a large area of measurement or a small area of measurement of the color sample, in accordance with the type of sample being measured and without frequently having to stop and recalibrate the instrument to the new aperture size;

Ability to verify/measure a wet formulated paint without having to wait for it to dry, so as to reduce instrument contamination;

Use of sealed optical systems within the chassis (no instrument contamination from checking wet paint samples);

Direct open air viewing with insensitivity to ambient light or sample depth variation (allows easy one-handed sample presentation);

Full spectrum LED based illumination (allows ambient light rejection for open air viewing and permits >10× reduction in required calibrations);

Ability to greatly reduce (or eliminate) factory service due to lamp aging or burnout, by virtue of the long life of the illuminator light source (e.g., LED cocktail 72);

Switchable measurement spot sizes without requiring a recalibration (allows fast and easy change of spot size to accommodate a broader variety of sample types);

Ability to minimize repair to mechanical parts; and

Other. For example, component life and a ecologically "green" system can be provided with reduced power consumption by providing automatic shutdown when not in use.

Preferred embodiments of the POP spectrophotometer 10 provide the features of (1) insensitivity of ambient light, (2) insensitivity to depth variation, and (3) precise active targeting. The term "non-contact" spectrophotometer, though used in many contexts, can specifically be used in the present application to refer to those embodiments of a POP spectrophotometer that possess all of the foregoing three enumerated characteristics. For example, in connection with a "non-contact" POP spectrophotometer and regarding ambient level insensitivity, a user is not restricted to taking measurements in a dark room, but, rather the user is free to openly view the color sample (illuminated by ambient as well as instrument light) while it is actually being measured. Regarding insensitivity to depth variation, in addition to facilitating easy location of samples in a target location $T_L$ of the X axis & Y axis of the target plane $T_P$, non-contact embodiments of the POP spectrophotometer also provide insensitivity to variation in the Z axis normal to that sample plane (e.g., depth D of FIG. 5). Insensitivity to depth variation within some measurement depth window is provided to accommodate variations in sample presentation to this open viewing environment. Regarding active targeting, such enables precise and easy identification of the target location $T_L$. Although a color sample may not reside in a traditional fixture, sample-holder, or template, it must enable the user to very precisely locate what part of the sample is to be measured, and do so with ease.

Thus, disclosed herein is a POP spectrophotometer for taking more accurate measurements for paint formulation, where the POP spectrophotometer allows for sample presentation, orientation, and measurement, preferably all in open view of the user. This greatly improves ease of use and offers the added robustness of no longer contaminating the measurement engine with wet paint during color verification of the formulated paint. Such enhancements to ease of use and robustness of unit also offer the possibility of customer initiated measurements, rather than measurements taken by trained store associates, eventually being used for paint formulation.

The examples presented herein are intended to illustrate potential and specific implementations of the present disclosure. It can be appreciated that the examples are intended primarily for purposes of illustration of the invention for those skilled in the art. No particular aspect or aspects of the examples are necessarily intended to limit the scope of the present invention.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that focused discussion on those elements known in the art would not facilitate a better understanding of the present invention, and therefore, a more detailed description of such known elements is not provided herein.

Any element expressed herein as a means for performing a specified function is intended to encompass any way of performing that function including, for example, a combination of elements that performs that function. Furthermore the invention, as may be defined by such means-plus-function claims, resides in the fact that the functionalities provided by the various recited means are combined and brought together in a manner as defined by the appended claims. Therefore, any means that can provide such functionalities may be considered equivalents to the means shown herein.

While various embodiments of the invention have been described herein, it should be apparent, however, that various modifications, alterations and adaptations to those embodiments may occur to persons skilled in the art with the attainment of some or all of the advantages of the present invention. The disclosed embodiments are therefore intended to include all such modifications, alterations and adaptations without departing from the scope and spirit of the present invention as set forth in the appended claims.

What is claimed is:

1. A housing assembly for a point-of-purchase spectrophotometer for open-viewing measurement of a color sample, comprising:
    support means at least partially defining a target plane with a target location; and
    a chassis in secured arrangement with said support means such that said chassis and support means are configured to, in use, space said chassis apart from the target plane for open-viewing of the target location, said chassis configured to position (i) an illumination line of sight of a first illumination optical system toward the target location at substantially about forty-five degrees with respect to the target plane, and (ii) an imaging line of sight of an imaging optical system toward the target location at substantially about ninety degrees with respect to the target plane;
    said chassis being further configured to position at least one additional line of sight comprising at least one of (i) a second illumination line of sight of a second illumination optical system toward the target location, at substantially about forty-five degrees with respect to the target plane, and at substantially about ninety degrees with respect to the illumination line of sight as measured about the imaging line of sight, (ii) a sheen line of sight of a sheen detection system toward the target location, at substantially about forty-five degrees with respect to the target plane, and at substantially about ninety degrees with respect the illumination line of sight, and (iii) a camera line of sight of a camera system toward the target location.

2. The housing assembly of claim 1 in combination with the illumination optical system and the imaging optical system.

3. The housing assembly of claim 1, wherein the at least one additional line of sight comprises the camera line of sight.

4. The housing assembly of claim 3 in combination with the camera system.

5. The housing assembly of claim 1, wherein the at least one additional line of sight comprises the second illumination line of sight.

6. The housing assembly of claim 5 in combination with the second illumination optical system.

7. The housing assembly of claim 1, wherein the at least one additional line of sight comprises the sheen line of sight.

8. The housing assembly of claim 7 in combination with the sheen detection system.

9. A point-of-purchase spectrophotometer for open-viewing measurement of a color sample, comprising:
    a plurality of optical systems having lines of sight directed toward a target location of a target plane, said optical systems providing depth-insensitivity associated with a depth;
    a housing assembly containing the optical systems and at least partially defining a position of the target plane, said housing assembly spacing apart said plurality of optical systems from the target plane; and
    an alignment device in secured arrangement with said housing assembly so as to be configured to be positioned between said plurality of optical systems and said target plane and to be spaced apart from the target plane by the depth, said alignment device defining an aperture proximal the target location.

10. The point-of-purchase spectrophotometer of claim 9, wherein said plurality of optical systems include an imaging optical system, an illumination optical system, and at least one additional optical system comprising at least one of a second illumination optical system, a sheen detection optical system, and a camera system.

11. The point-of-purchase spectrophotometer of claim 9, wherein said alignment device includes a calibration plate assembly, said calibration plate assembly being movable between a first position for providing a reflective surface proximal the target location to facilitate calibration of at least one of the plurality of optical systems and a second position in which the lines of sight are unobstructed by the calibration plate.

12. The point-of-purchase spectrophotometer of claim 9, wherein said housing assembly includes a chassis containing said plurality of optical systems and support means for spacing said chassis apart from the target plane for open viewing of the target location.

13. The point-of-purchase spectrophotometer of claim 9, wherein said plurality of optical systems are configured to provide ambient light insensitivity.

14. A point-of-purchase spectrophotometer for open-viewing measurement of a color sample, comprising:
- an illumination optical system having an illumination line of sight directed toward a target location of a target plane; and
- an imaging optical system having an imaging line of sight directed toward the target location;
- wherein the imaging optical system includes a targeting optical system for (i) defining a perceived target size associated with the target location, and (ii) projecting light toward the target plane to define a size of the target location for user-identification thereof; and
- wherein the targeting optical system includes a switchable aperture assembly.

15. The point-of-purchase spectrophotometer of claim 14, wherein said targeting optical system has a line of sight in substantial alignment with the imaging line of sight.

16. The point-of-purchase spectrophotometer of claim 14, wherein said switchable aperture assembly of the targeting optical system includes a first aperture of a first size and a second aperture of a second size unequal to said second size, and wherein said switchable aperture assembly is movable at least between a first position, at which said first aperture is positioned at the imaging line of sight at the image plane, and a second position, at which said second aperture is positioned at the imaging line of sight at the image plane, said first and second apertures functioning as field stops that define the perceived target size associated with the target location.

17. The point-of-purchase spectrophotometer of claim 16, wherein said targeting optical system includes (i) a targeting light source configured to be positioned between the target plane and said switchable aperture assembly in alignment with the imaging line of sight, (ii) a first reflecting ring associated with and proximal to said first aperture and having a first ring size, and (iii) a second reflecting ring associated with and proximal to said second aperture and having a second ring size unequal to said first ring size, wherein said first and second rings are configured to reflect light from said targeting light source toward the target plane so as to define the size of the target location.

18. The point-of-purchase spectrophotometer of claim 17, wherein said first reflecting ring at least partially defines said first aperture.

19. The point-of-purchase spectrophotometer of claim 14, wherein said illumination optical system and said imaging optical system are configured to provide depth insensitivity.

20. The point-of-purchase spectrophotometer of claim 14, wherein said illumination optical system and said imaging optical system are configured to provide ambient light insensitivity.

* * * * *